United States Patent
Rand et al.

(10) Patent No.: US 6,208,711 B1
(45) Date of Patent: Mar. 27, 2001

(54) METHOD AND APPARATUS FOR CLEARING IONS IN A SCANNING ELECTRON BEAM COMPUTED TOMOGRAPHIC SYSTEM USING A SINGLE POTENTIAL POWER SOURCE

(75) Inventors: Roy E. Rand, Palo Alto; Khem Garewal, San Ramon; James F. Heilman, San Jose, all of CA (US)

(73) Assignee: Imatron, Inc., South San Francisco, CA (US)

( * ) Notice: Subject to any disclaimer, the term of this patent is extended or adjusted under 35 U.S.C. 154(b) by 0 days.

(21) Appl. No.: 09/399,910

(22) Filed: Sep. 21, 1999

(51) Int. Cl.$^7$ ....................................... H01J 35/14
(52) U.S. Cl. .................. 378/138; 378/4; 378/137; 378/131
(58) Field of Search .................. 378/138, 137, 378/4, 121, 13, 119

(56) References Cited

U.S. PATENT DOCUMENTS

| | | | |
|---|---|---|---|
| 5,193,105 | * | 3/1993 | Rand et al. ........................... 378/137 |
| 5,289,519 | * | 2/1994 | Rand ........................................ 378/4 |
| 5,719,914 | * | 2/1998 | Rand et al. .............................. 378/4 |

* cited by examiner

Primary Examiner—Robert Kim
Assistant Examiner—Pamela R. Hobden
(74) Attorney, Agent, or Firm—Flehr Hohbach Test Albritton & Herbert LLP (57) ABSTRACT

In a scanning electron beam CT system, a positive ion clearing electrode system is disposed within the CT system solenoid coil, and is operated from a single power source. Mounted coaxially about the electron beam, preferably the electrode system includes three sections, each having two electrode elements, one element being coupled to about −800 V to about −2 kV and the other element being grounded. Within the electrode system, the ratio between element diameter and electron beam diameter is substantially constant. Preferably elements are helically twisted about the beam axis. The electrode configuration cancels net quadrupole (focusing) and octopole (aberration-producing) fields. In the presence of electric discharge, essentially zero electron beam displacement and deflections occurs, and changes in focusing strength remain zero.

20 Claims, 10 Drawing Sheets

METHOD AND APPARATUS FOR CLEARING IONS IN A SCANNING ELECTRON BEAM COMPUTED TOMOGRAPHIC SYSTEM USING A SINGLE POTENTIAL POWER SOURCE

Field of the Invention

The present invention relates generally to scanning electron beam systems for X-ray production in a computed tomography X-ray transmission system, and more particularly to reliably controlling uniformity of the beam space-charge density, preferably by extracting positive ions.

BACKGROUND OF THE INVENTION

Scanning electron beam computed tomography systems are described generally in U.S. Pat. No. 4,352,021 to Boyd, et al. (1982). The theory and implementation of devices to help control the electron beam in such systems is described in detail in U.S. patents to Rand et al. U.S. Pat. Nos. 4,521,900 (1985), 4,521,901 (1985), 4,625,150 (1986), 4,644,168 (1987), 5,193,105 (1993), and 5,289,519 (1994). Applicants refer to and incorporate herein by reference each said patent to Boyd et al. and to Rand et al.

Figure 1:
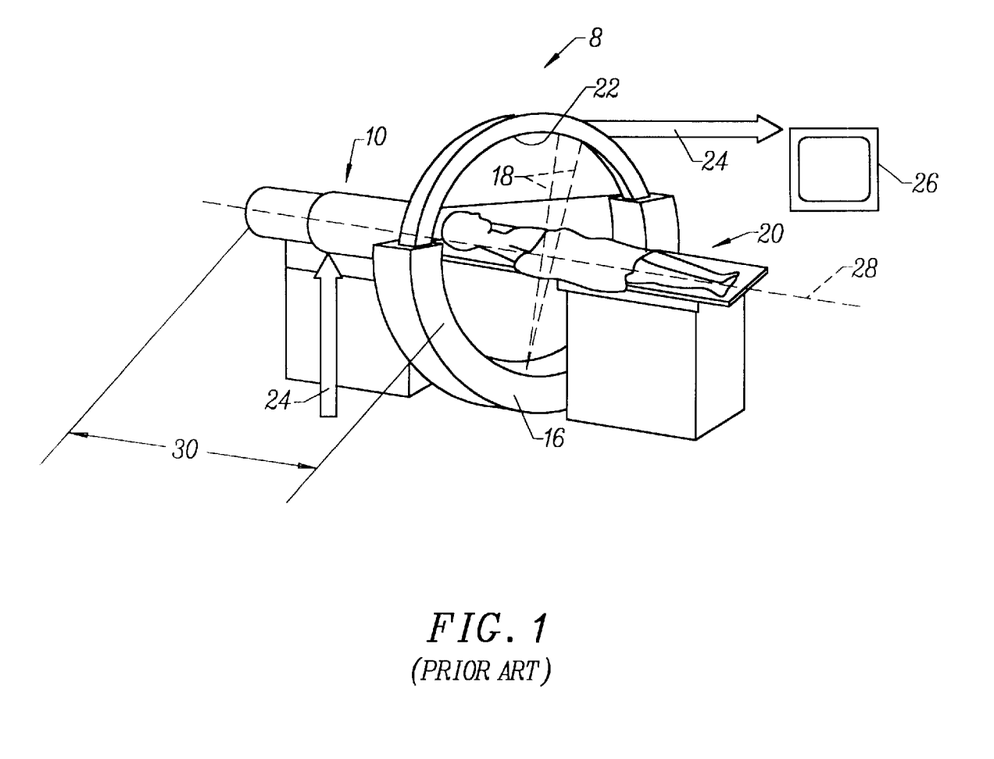
FIG. 1 depicts a generalized prior art scanning electron beam computed tomography X-ray system, with which the present invention may be practiced.
Figure 2:
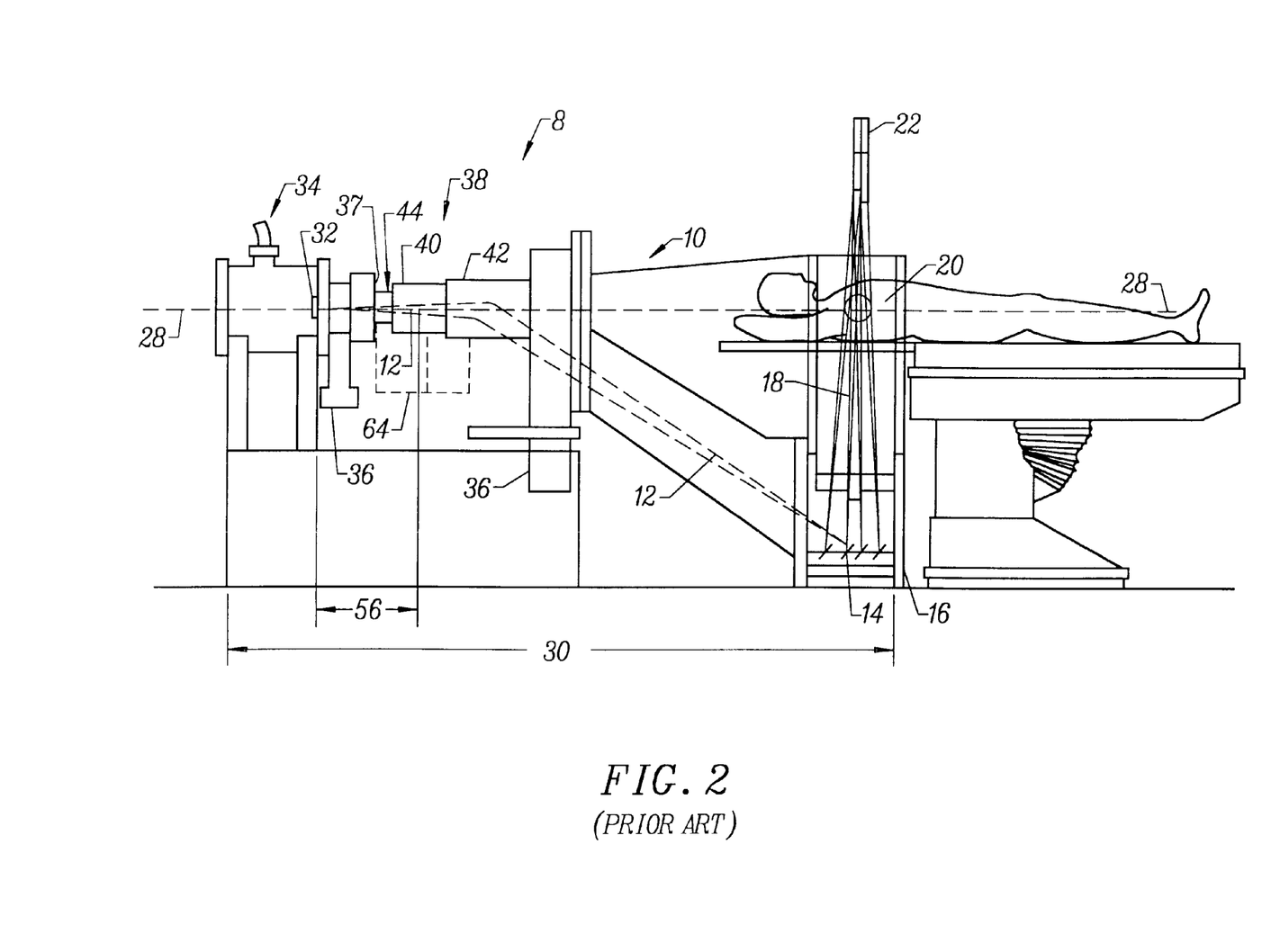
FIG. 2 is a longitudinal view of the system shown in FIG. 1.

As shown in FIGS. 1 and 2 and as described in detail in U.S. Pat. No. 4,521,900 to Rand et al., a generalized computed tomography X-ray transmission scanning system 8 includes a vacuum housing chamber 10 wherein an electron beam 12 is generated. The electron beam is caused to scan at least one circular target 14 located within front lower portion of chamber 16.

Upon striking the target, the electron beam emits a moving fan-like beam of X-rays 18. The X-rays pass at least partially through a region of a subject 20 (e.g., a patient or other object) and register upon a region of a detector array 22 located diametrically opposite. The detector array outputs data to a computer processing system (indicated by arrows 24) that processes and records the data. The computer processing system then reconstructs or produces an image of a slice of the subject on a video monitor 26. As indicated by the second arrow 24, the computer processing system also controls the scanning system and its production of the electron beam. By repeating the scanning process after the patient has been moved laterally along chamber Z-axis 28, a series of X-ray images representing axial "slices" of the patient's body is produced.

Referring to FIG. 2, more specifically, electron gun 32 is disposed within extreme upstream end 34 of chamber (or "drift tube") 10, which chamber may be as long as about 3.8 m in some prior art configurations. A sufficiently long drift tube permits the electron beam to expand and become more uniform, and can promote electron beam space-charge homogenization by evening out electron distribution.

In response to high voltage excitation (e.g., 130 kV) the electron gun produces electron beam 12. The high voltage electron gun potential accelerates the electron beam downstream along a first straight line path defining the chamber Z-axis. A beam optical system 38 typically includes a focus coil 40 and dipole and quadrupole coils 42, and is mounted downstream on chamber 10. Coils 40 and 42 respectively magnetically focus and shape and scan the beam 12 typically about 210° in a scan path across the arc-like ring target 14.

Although vacuum pump 36 evacuates chamber 10, residual gases inevitably remain that produce positive ions in the presence of the electron beam. Gases may also be introduced into the chamber for the purpose of producing positive ions, since the ions are beneficial in the downstream chamber region.

The electrons are negatively charged and the resultant space-charge causes the electron beam to diverge or expand in the upstream chamber region between the electron gun and the focus and deflection coils. This upstream region expansion is beneficial because the beam width at the target varies approximately inversely with the beam diameter at the focus and deflection coils. However the positive ions that are created can detrimentally neutralize the space-charge, preventing electron beam divergence in the chamber upstream region. Unless counteracted, this can increase beam width at the target, resulting in a defocused X-ray image. Neutralization can also result in the electron beam becoming unstable and even collapsing completely.

In the chamber region downstream from the focus and deflection coils, a converging electron beam is desired. Here the beam preferably is neutralized by positive ions produced by the electrons from residual gas in the chamber, or from a gas purposely introduced into the chamber. The neutralization eliminates electron self-repulsion, while the beam's attractive magnetic field converges and self-focuses the beam. As a result, the beam can self-focus sharply upon the target to produce a sharp X-ray image. Elements of the beam optical system fine tune the converged beam to produce a sharp X-ray image.

Ideally, the electron beam would exhibit uniform current density, diverging upstream and converging to sharply self-focus downstream. An electron beam with a uniform electron distribution can act as its own perfect lens: self-diverging in the upstream chamber region and self-converging in the downstream chamber region to focus sharply on the target. A uniform space-charge density is desired because any optical aberrations due to the electron beam self-forces would then be eliminated. In addition to degradation from ions, the electron beam space-charge density may not be perfectly uniform due to imperfections in the electron gun and in the beam optics system.

Understandably, achieving a perfectly uniform space-charge density is difficult. For example, electron gun imperfections cause the electron beam to have a non-uniform space-charge density in a plane perpendicular to the Z-axis 28. Housing discontinuities 37 create gaps that prevent conventional ion clearing devices from subjecting the electron beam to an electric field in the upstream region. In compact systems, drift distance between the electron gun and the beam optics is relatively short, e.g., 40 cm or so, and the electron beam has insufficient time for its space-charge density to become sufficiently homogeneous.

Figure 3:
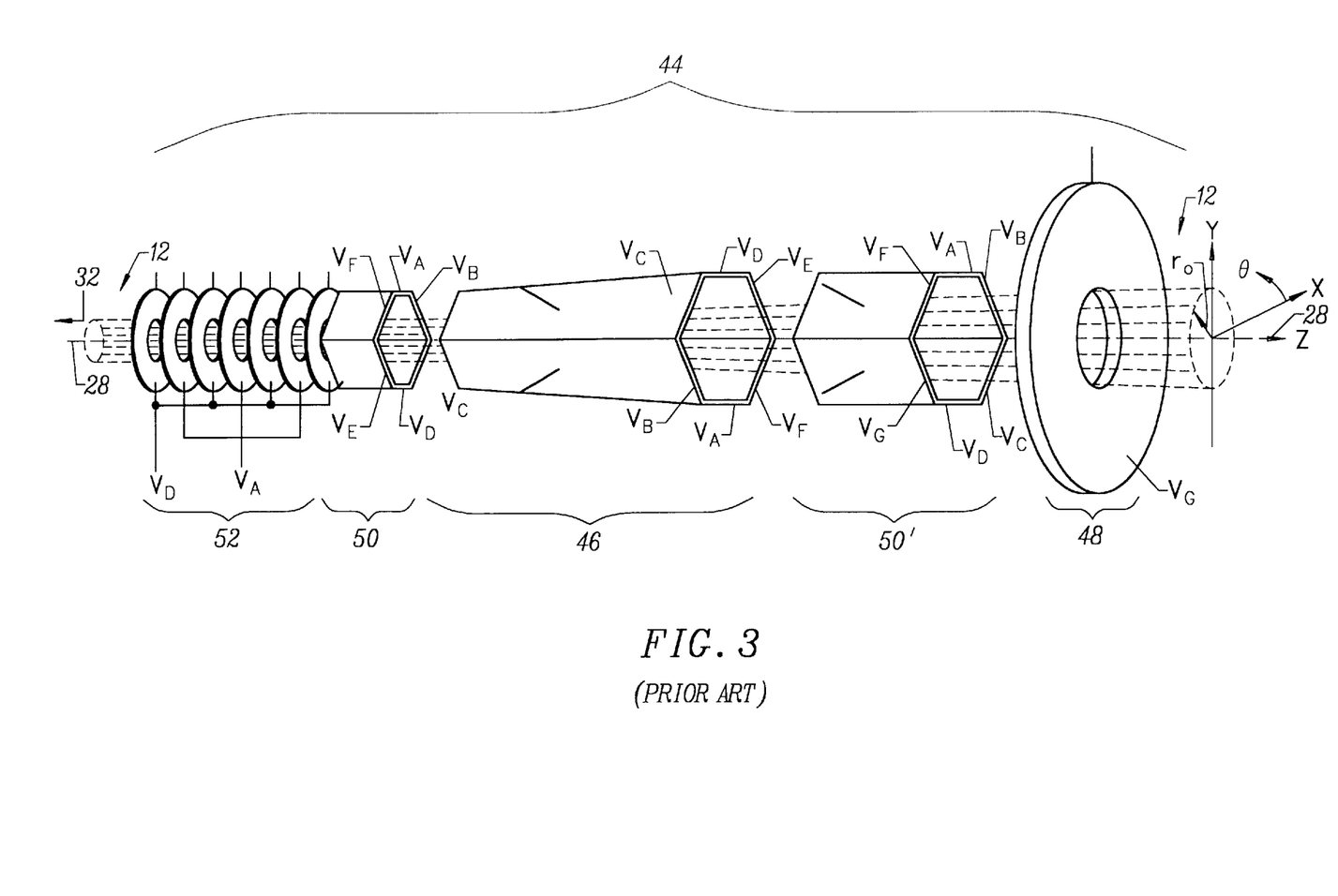
FIG. 3 is a perspective view of an ion clearing electrode assembly, according to the prior art.

Various specific ion controlling electrode assembly configurations were described in above-referenced U.S. patents to Rand et al. For example, FIG. 3 is a simplified depiction of ion controlling electrode assembly 44, based upon U.S. Pat. No. 5,289,519. This electrode assembly improves space-charge density and promotes sharp focusing of a high resolution X-ray image produced by system 8. Assembly 44 included a multi-sided rotatable field ion clearing electrode 46 ("RICE"), a washer-like positive ion electrode 48 ("PIE"), first and second multi-sided ion clearing electrodes 50, 50' ("ICE"), and a periodic axial field ion controlling electrode 52 ("PICE"), although not all of these elements were necessarily required. PICE 52 comprises a series of washer-like disks with alternate disks being connected to a common power source. The various RICE, PIE, ICE and PICE elements comprising assembly 44 preferably were stainless steel and were mounted within chamber 10 using insulated standoffs.

Electrode assembly 44 was mounted between electron gun 32 and beam optical assembly 38 within housing 10, with electron beam 12 passing axially through assembly 44 along Z-axis 28. Ideally Z-axis 28 is coaxial with electron beam 12 upstream from the beam optics assembly 38, and with both the longitudinal chamber axis and the axis of symmetry for electrode assembly 44 and beam optics assembly 38.

Typically elements comprising assembly 44 were coupled to one of several various sources of potential, e.g., Va, Vb, Vc, Vd, Ve, Vf, Vg. Typical values for these potentials were Va=0 V, Vb=−0.25 kV, Vc=−0.75 kV, Vd=−1 kV, Ve=−0.75 kV, Vf=−0.25 kV, and Vg=2 kV, In practice, the maximum potential Vd (which is −1 kV in the above example) could be between perhaps −0.8 kV and about −2 kV, with Vd, Vb, Vc, Ve, and Vf being scaled down or up proportionally.

These various potentials create transverse uniform electric fields to which the electron beam is subjected. Electric field non-uniformities, which may be represented by a multipole expansion, cause aberrations in the electron beam optics, to the detriment of the images produced by the overall system. The geometry of the three sets of electrodes and the applied potentials are selected to render zero the quadruple, sextupole, and octopole electric fields. As a result, the lowest order multipole electric field present is the decapole, which has minimal effects upon the electron beam.

Figure 4A:
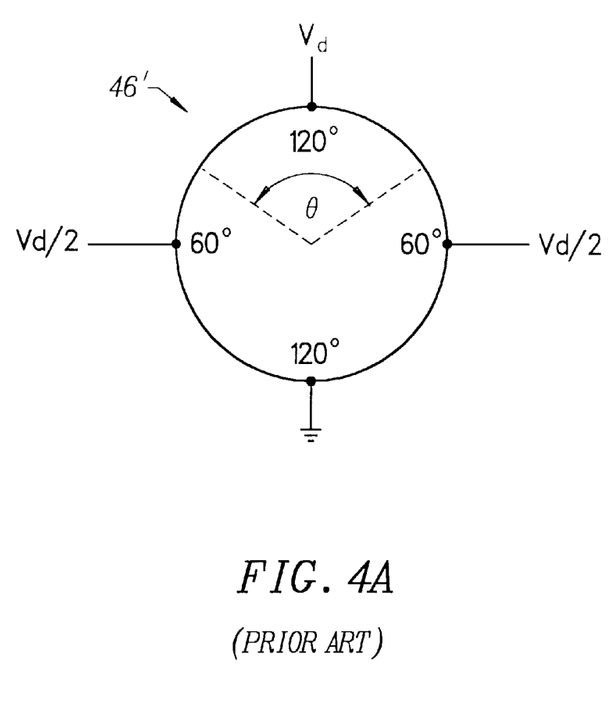
FIGS. 4A and 4B depict alternate prior art ion clearing electrode configurations and bias potentials, according to the prior art.
Figure 4B:
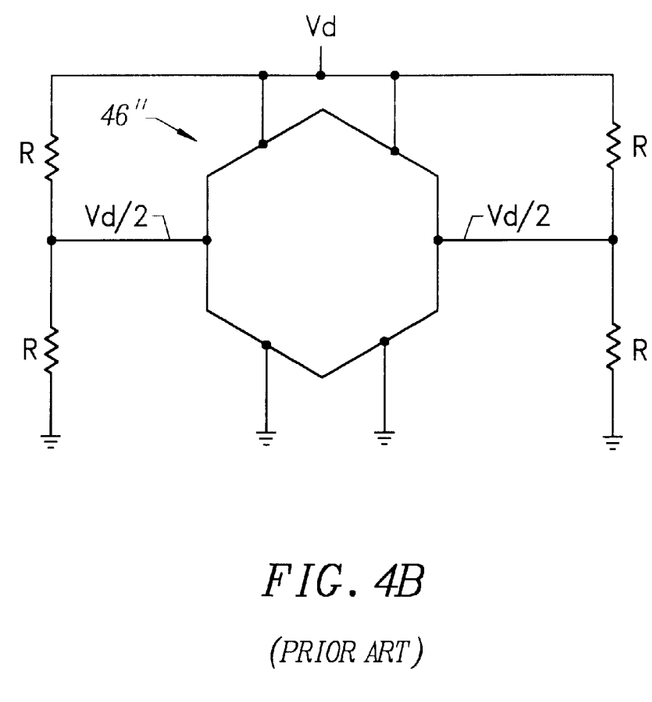

Other electrode configurations are possible, for example those shown by electrode assemblies 46' and 46" in FIGS. 4A and 4B, respectively. Again, these assemblies produce a transverse uniform electric field. At any cross section, three sets of electrodes are present, energized at a nominal voltage Vd, Vd/2, and ground, where Vd is in the range of about −800 V to about −2 kV.

In general, as set forth in U.S. Pat. No. 5,239,519, dipole electric fields may be set to alternate in direction along the beam axis to minimize (but not completely eliminate) net deflection of the electron beam.

In viewing the configurations of FIGS. 3, 4A, and 4B, it is seen that multiple potentials are required. The requirement for multiple sources of operating potential, or (as shown in FIG. 4B) for divider circuitry to create multiple potentials is disadvantageous. It is inevitable with known ion clearing electrode systems that electric discharges will appear, with resultant inter-electrode voltage breakdown. When a discharge occurs the voltage on an electrode can change within microseconds to zero volts or to the voltage of an adjacent electrode, and can recover within milliseconds. Such electrode potential transients can affect the electron beam in several ways, none of which is beneficial to safe operation of the overall system.

Firstly, the potential change will deflect the electron beam because prior art electrode system are not truly non-deflecting in the presence of the beam-optical system solenoidal magnetic field. The deflected electron beam will not be on the axis of the beam-optical system after leaving the ion-clearing region. This can accentuate aberrations due to the final state of the ion-clearing device, or the downstream electron beam-optical components. Further, electrode discharge can interrupt uniform movement of the electron beam spot along the X-ray emitting target, perhaps momentarily slowing the traverse speed. The typically tungsten target surface can be seriously damaged by the decreased scan speed, and artifacts can appear in the reconstructed CT image. Even after the system recovers electrically, permanent damage to the tungsten target may have occurred, which will produce further artifacts.

Secondly, during a discharge the relative potentials of the various electrodes can change by different amounts, which will cause the electric field to become non-uniform. For example, one set of electrodes may short rapidly to ground potential while other electrodes might remain initially unaffected by the discharge. Further, the resistor-capacitor (RC) time constant associated with various sets of electrodes may differ, such that some electrodes will recover to their desired potential sooner than other electrodes. Resultant non-uniformities in the electric fields can generate quadrupole fields, which can unsafely focus the electron beam and cause damage to the tungsten target. Further, quadrupole and high order multipole fields can cause artifacts in the recovered CT system image.

In addition to such performance degradation, the requirement for separate power sources (FIGS. 3, 4A) or at least resistive voltage dividers (FIG. 4B) adds to the cost of the overall system. Further, reliability is compromised by the need to bring multiple electric feedthroughs into the vacuum chamber to couple the various potentials to ion clearing electrode system electrodes.

In summary, there is a need in electron beam scanner systems for a method and apparatus to remove positive ions, to prevent their neutralizing electron beam space-charge necessary to overcome upstream self-focusing. Such an ion clearing electrode method and apparatus should extract positive ions using electrostatic fields created from a single power source. Preferably the ion clearing electrode system should promote safe focusing regimes of the electron beam.

SUMMARY OF THE INVENTION

Positive ions are extracted from the electron beam of an electron beam computed tomography scanner system using a an ion clearing electrode assembly that is operable from a single source of operating potential and produces zero net beam deflection and displacement. The single potential source advantageously contributes to safe operation of the system and to a simpler design. As used herein, the single power source had two output leads with potential V1 (preferably about −800 V to about −2 kV) and potential V2 (preferably ground). The single potential electrode system is normally installed inside a magnetic solenoid (focusing) lens, concentric about the scanner system Z-axis, and uses two basic arrays of electrode cross-sections that alternate along the Z-axis.

At each cross-section of the electrode assembly two electrode elements or members are present, one electrode from a first array and one electrode from a second array. At each cross-section, one electrode member defines an arc length of substantially 120°, and the other electrode member defines a complementary arc length of substantially 240°. At each cross-section, one electrode member is coupled to V1 and the complementary electrode member is coupled to V2. The complementary arc lengths are chosen such that sextupole electric field strengths are essentially zero.

The electric field needed for ion extraction and for cancellation of field effects upon the beam should be inversely proportional to beam radius. Accordingly, at each cross-section the ratio between electrode element radius to electron beam radius is substantially constant. This constant ratio may be achieved using generally cylindrical electrode cross-sections whose radii increase step-wise along the system axis, or using conical electrode cross-sections whose radius increases continuously along the system axis.

Along the length of the electrode assembly, adjacent electrode members may have complementary arc lengths and coupled to the same power lead, for example 240° arc coupled to V1, with the adjacent (in a lengthwise sense) electrode member having a complementary 120° arc and also coupled to V1. In cross-section, the 240° arc electrode member would be complemented by a 120° arc electrode member coupled to V2, and the 120° arc electrode member would be complemented by a 240° arc electrode member also coupled to V2. This alternating arc length configuration alternates and thereby cancels the effects of quadrupole and octopole electric fields in lengthwise successive electrode sections without alternating the dipole fields responsible for electron beam deflection. This configuration may be advantageously implemented using pairs of electrode members with crenellated edges.

Elsewhere along the length of the electrode assembly, lengthwise adjacent electrode sections may have the same arc length but are coupled to opposite power supply leads. Thus a first cross-section might have a 240° arc electrode element coupled to V1 and a complementary 120° arc electrode element coupled to V2. The lengthwise adjacent cross-sections would provide 240° arc electrode element (adjacent the first 240° arc electrode element) coupled to V2, and a complementary 120° arc electrode element coupled to V1. This implementation cancels the effects of dipole as well as quadrupole and octupole electric fields in lengthwise successive electrode sections.

Being surrounded by a solenoidal magnetic focusing lens, the beam electrons will describe helical trajectories. Accordingly, a preferred embodiment employs electrode sections having crenellated edges to provide the above-described cancellation of quadrupole and octopole fields. These edges are progressively twisted in their orientation to follow such trajectories, with greater twist being imparted to cancellations and electrodes further downstream than upstream. In this preferred embodiment, lengthwise adjacent electrode sections that coupled to opposite power source leads have like arc lengths. This configuration effectively cancels net quadrupole (focusing) and octopole (aberration-producing) fields, and produces zero net electron beam displacement and deflection.

Because all energized electrodes are directly connected to each other, all multipole fields remain strictly proportional during any electric discharges. Thus, net displacement and deflection of the electron beam, and changes in focusing strength remain zero. As the electron beam emerges from the present invention precisely on-axis, effects of aberrations due to downstream beam-optical components are minimized. In this fashion, a single power supply advantageously is used to clear positive ions in a fashion that results in net zero electron beam distortion due to integrated multipole fields.

Other features and advantages of the invention will appear from the following description in which the preferred embodiments have been set forth in detail in conjunction with the accompanying drawings.

DESCRIPTION OF THE PREFERRED EMBODIMENTS

As will now be described, the present invention provides an electrode assembly that surrounds and subjects an electron beam to electric fields transverse to its velocity that advantageously extract positive ions from the electron beam with essentially no net beam deflection. At the downstream end, the electron beam exits the electrode assembly on-axis, thus minimizing the distortions due to downstream beam optical systems.

Figure 5A:
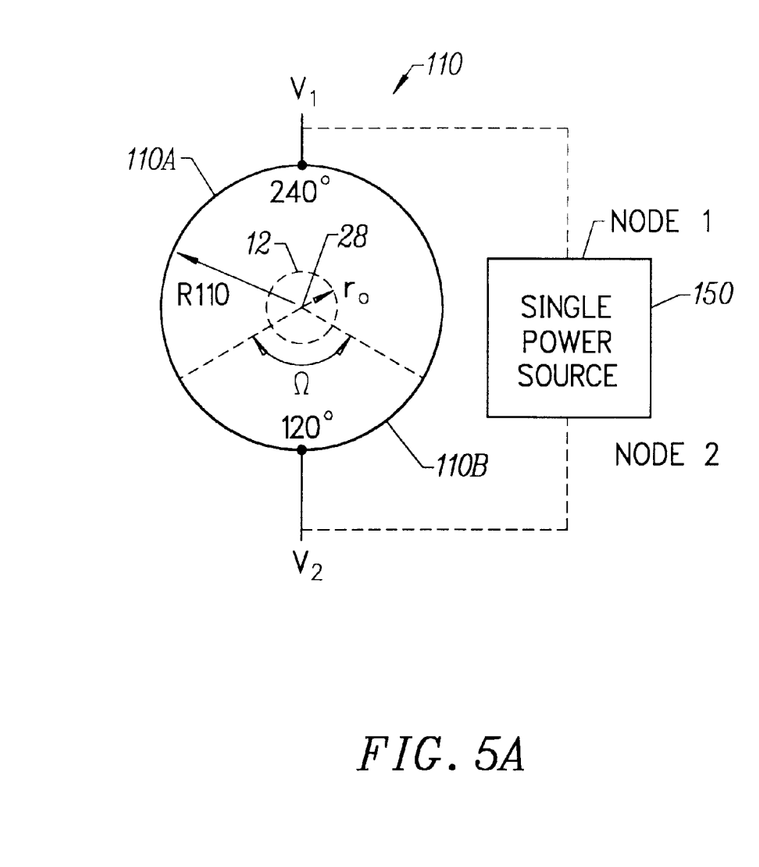
FIGS. 5A and 5B are cross-sections depicting 120° and 240° element arrays coupled to a single power source, according to the present invention.

FIG. 5A depicts a cross-section of a portion of such an electrode assembly 110 used to extract positive ions from the electron beam of an electron beam computed tomography scanner system, such as system 8 in FIG. 1. Electrode assembly 110 is disposed coaxially along system Z-axis 28 preferably within the geometry of the scanner system solenoid coil system 40, upstream from a PIE-type electrode 48.

In the cross-section of FIG. 5A, generally cylindrical first element 110A and generally cylindrical second element 110B are each symmetrically located about system axis 28. In the preferred embodiment, at each cross-section one element defines a greater arc length than the other, namely an effective 240° arc for first element 110A, and an effective 120° arc for second element 110B. Complementary electrode arc lengths of 120° and 240° were selected to produce electric fields from a single power source that would extract positive ions with zero sextupole field component.

Figure 5B:
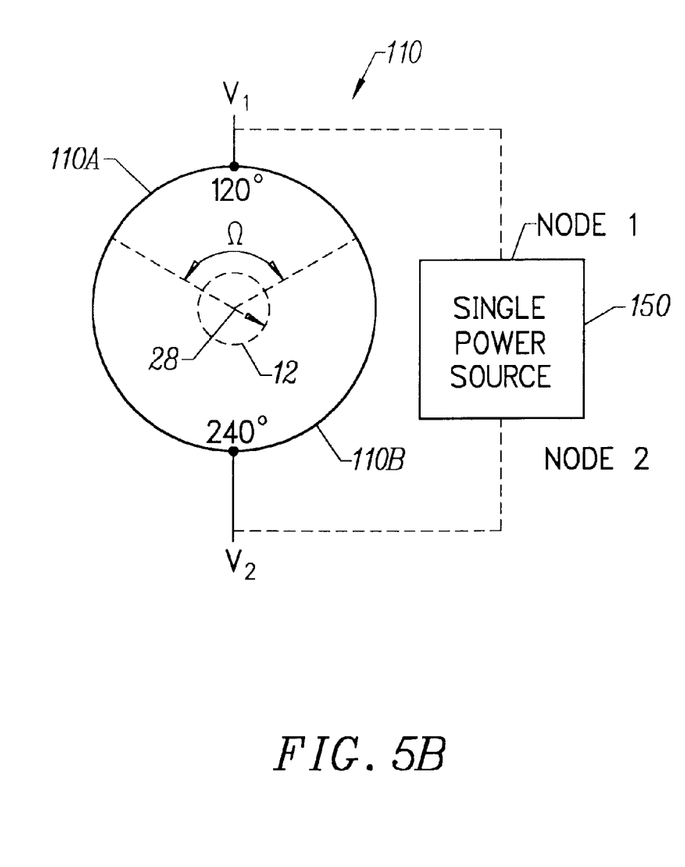

The configuration of FIG. 5B may be used in lieu of FIG. 5A or may represent an adjacent, downstream, sub-section of the same ion clearing electrode. Note that whereas in FIG. 5A, the uppermost 240°-subtending electrode 110A is coupled to a power node V1, in FIG. 5B, the uppermost electrode 110A now subtends only 120° and is still coupled to power node V1. At the same time, in FIG. 5B, lower electrode section 110B now subtends an arc of 240° and is coupled to power node V2 whereas in FIG. 5A, the lowermost electrode 110B subtended only 120° and was coupled to power node V2.

In practice, V1 and V2 are the two output nodes of a single power supply 150, where V1 may be in the range of about −800 V to −2 kV and where V2 preferably is ground, e.g., 0 V. It will be appreciated in FIGS. 5A and 5B that the V1 and V2 connections may be exchanged. Thus in FIG. 5A, V2 and V1 could be coupled respectively to 240° and 120° arc length electrodes 110A, 110B, and in FIG. 5B, V1 and V2 could be coupled respectively to 240° and 120° arc length electrodes 110B, 110A.

A lengthwise combination of configurations with alternating potentials may establish and subject the electron beam to desired transverse electric fields that will advantageously extract positive ions from the electron beam with essentially no net deflection or displacement of the beam.

In some applications V2 (or V1) may be floated by some potential Vx about ground, in which case V1 (V2) would also be increased in magnitude by the same Vx. The smallest required magnitude for (V1–V2) will be determined by the magnitude of the minimum electric field necessary to extract ions from the electron beam, and by the electrode radii. The minimum electric field that is needed depends upon electron beam parameters such as beam current, electron velocity, and electron beam radius.

Although FIGS. 5A and 5B depict elements having the same radius, e.g,. R110, in practice at any location along Z-axis 28, the ratio between ion clearing electrode radius and electron beam radius $r_o$ will be constant. Since electron beam radius $r_o$ increases in the downstream direction, preferably the electrode radius increases in the same ratio.

Thus, in one embodiment sections of the present invention are formed with conical sections, and in the alternative embodiment cylindrically formed sections are used, with successive sections having greater (but constant) radius.

Figure 6A:
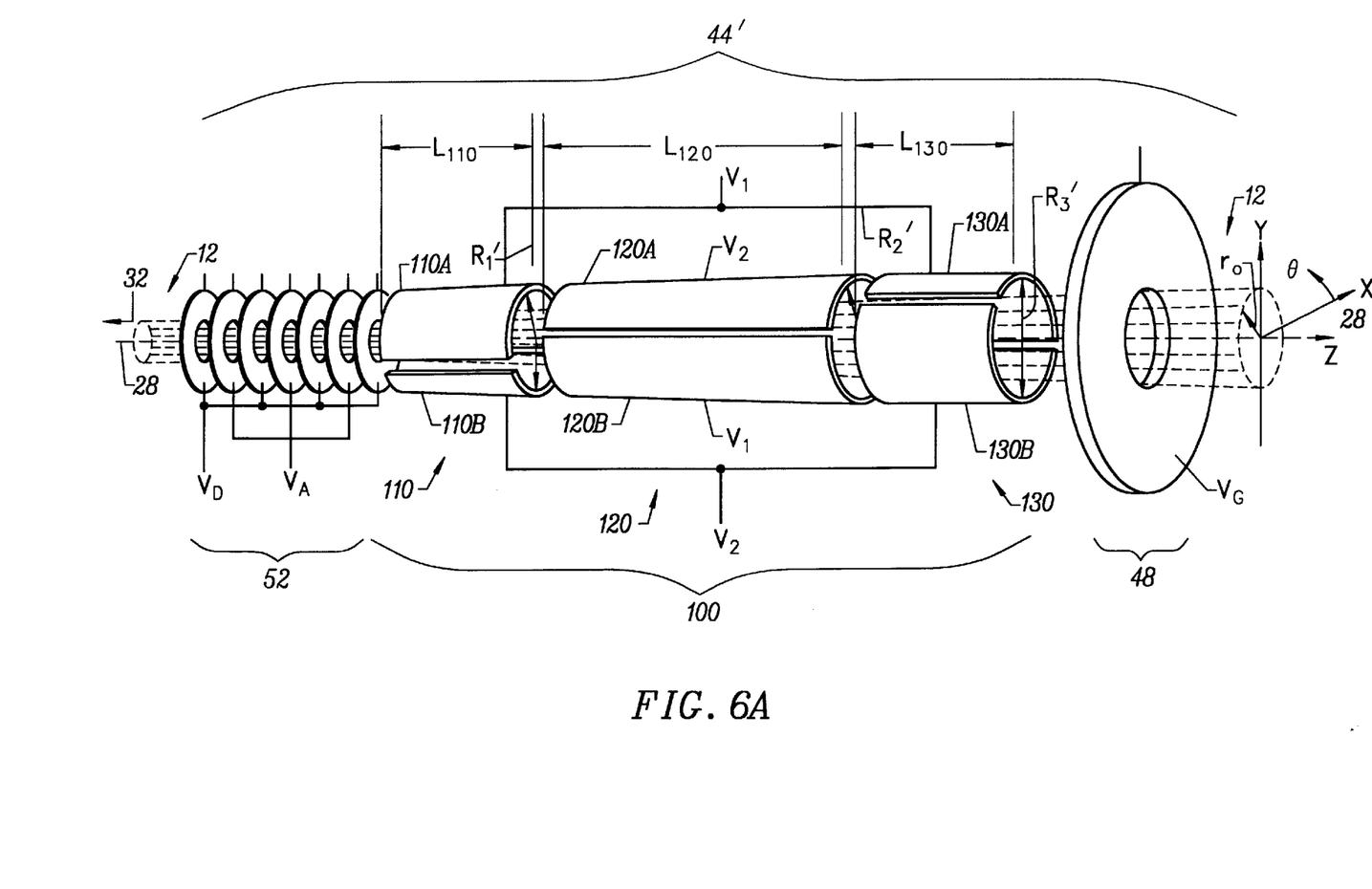
FIG. 6A is a perspective view of a coinically shaped ion clearing electrode assembly comprising three sections of helically twisted element arrays, according to the present invention.

FIG. 6A is a perspective view of a positive ion clearing electrode system 100, according to the present invention, used as part of an ion controlling electrode assembly 44'. Electrode system 100 preferably comprises three sections, denoted 110, 120, 130, having respective lengths L110, L120, L130, although more sections could instead be used.

As shown in FIG. 6A, electron beam 12 increases in diameter in the downstream (left-to-right) direction. Accordingly, electrode system 100 sections 110, 120, 130 are generally conical in shape, with element radii that increase as one goes in the downstream direction. In the conically configured system of FIG. 6A, the ratio of an element radius R (e.g., R1' or R2' or R3') to the electron beam radius $r_o$ within the element is approximately constant. Implementing electrode system 100 with a number of separate sections (three sections being shown in FIG. 6A) permits changing the diameter of each section to conform to the electron beam size. If cylindrically shaped electrodes were used instead of conically shaped electrodes, there would be a stair-step like increase in electrode radius R going from left-to-right in FIG. 6A such that $R/r_o$ was substantially constant.

Using several sections also facilitates the creation of alternating electric fields to ensure that the electron beam does not stray unacceptably far from the Z-axis and exits the system precisely on-axis. Also, it is desired that electrode assembly 100 continuously cancel the effects on the beam of at least quadrupole and octopole components in the electric fields, thus minimizing electron beam distortion. This cancellation is achieved by alternating sections along the axis with respect to either arc length or potential.

According to the present invention, electron beam deflection in one section of system 100 is essentially cancelled by beam deflection in another section such that the electron beam exits section 130 with substantially no net deflection. In the three-section embodiment of FIG. 6A, center section 120 has a length L120 that is approximately the sum of length L110 of section 110 and length L130 of the downstream section 130. This approximate L120≈L110+L130 relationship is predictable from modeling, and functioned best in operation to ensure that the electron beam exits electrode system 100 on-axis. In the preferred embodiment, L110≈4.7 cm, L130≈8.7 cm, and L120≈14.2 cm.

System 100 may be defined as including an array of first electrode elements 110A, 120B, 130A, and an array of second electrode elements 110B, 120A, 130B, each electrode element being coaxially symmetrical about Z-axis 28. In this configuration, electrode elements 110A, 120A, 130A have 120° arc lengths, and electrode elements 110B, 120B, 130B have complementary 240° arc lengths. The arc lengths could, however, be reversed such that elements 110A, 120A, 130A had 240° arc lengths, and elements 110B, 120B, 130B had 120° arc lengths. The remaining up stream and downstream elements, to the left and to the right of system 100, shown in FIG. 6A may be as described 1with respect to the prior art configuration of FIG. 3.

Note that in cross-section, system 100 will include one first electrode element member and one second electrode element member, and that one of the members will be coupled to power supply or power supply node V1, while the other member in the cross-section will be coupled to the other power supply node V2, preferably ground. As seen in FIGS. 5A and 5B, at a given cross-section, the two electrode element members have complementary arc length: one element member defines preferably 240° arc length, and the other element member preferably defines 120° arc length.

In reality, since the electrode system is normally fully or at least partially installed inside a magnetic solenoid focusing lens, electrons in the electron beam will describe helical trajectories. Accordingly, to provide true zero deflection and zero displacement of the electron beam, electrode sections are generally and progressively helically twisted along the system Z-axis.

Figure 6B:
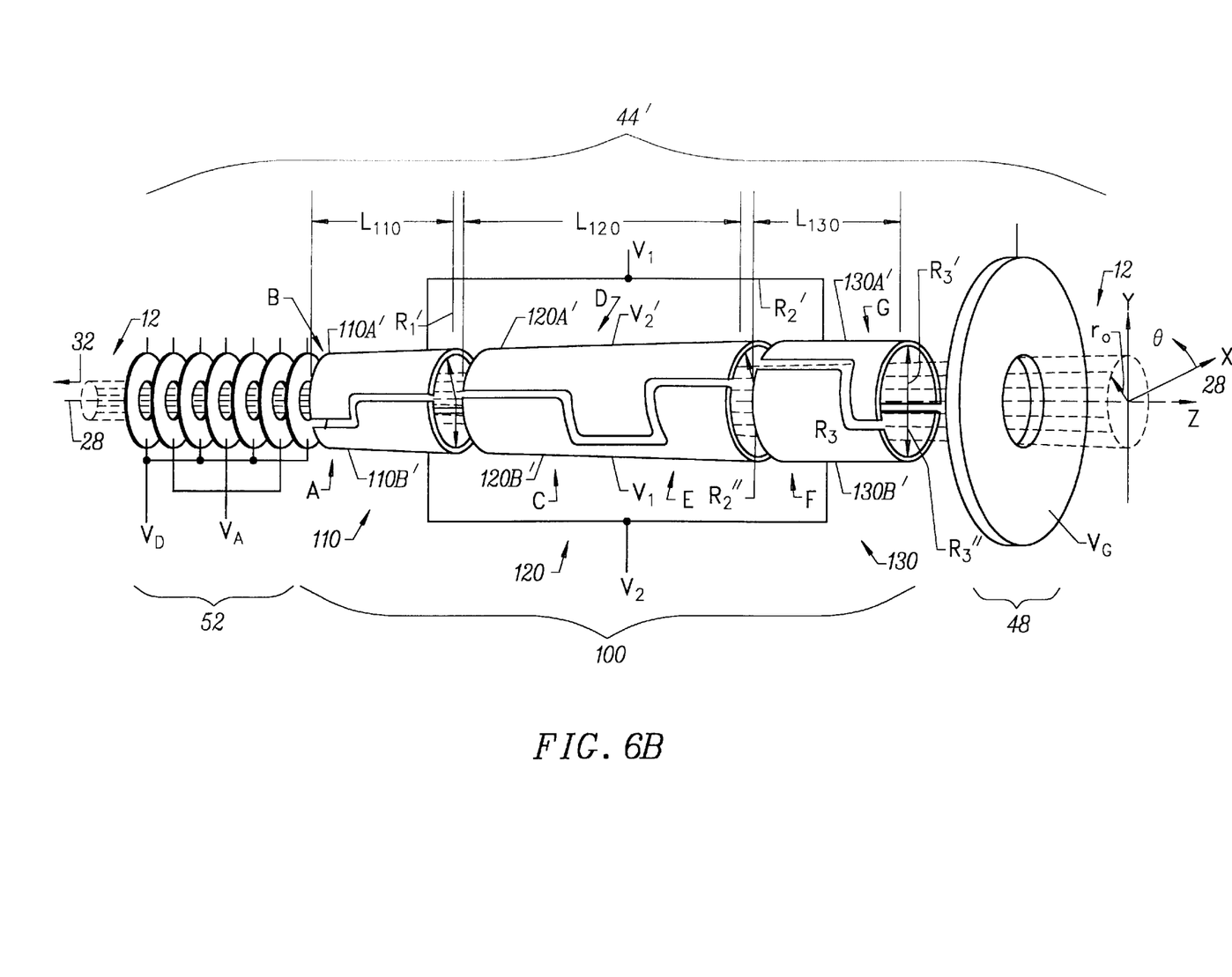
FIG. 6B is a perspective view of a conically stepped ion clearing electrode assembly comprising three sections of helically twisted crenellated sub-sectioned element arrays, according to the present invention.

A second embodiment of electrode system 100 is that shown in FIG. 6B. This embodiment provides preferably crenellated electrode sub-sections that are generally and progressively helically twisted along the system Z-axis. Lengthwise adjacent electrode sections have like arc length but are coupled to opposite power supply leads. The crenellated electrode sections present a twisted displacement that follows the generally helical trajectories of the electrons passing through the system solenoid. The resultant configuration of FIGS. 6A and 6B provide single potential electrode systems that operate within the magnetic field of the system solenoid coil to clear ions, while producing no net offset in the electron beam.

Figure 6C:
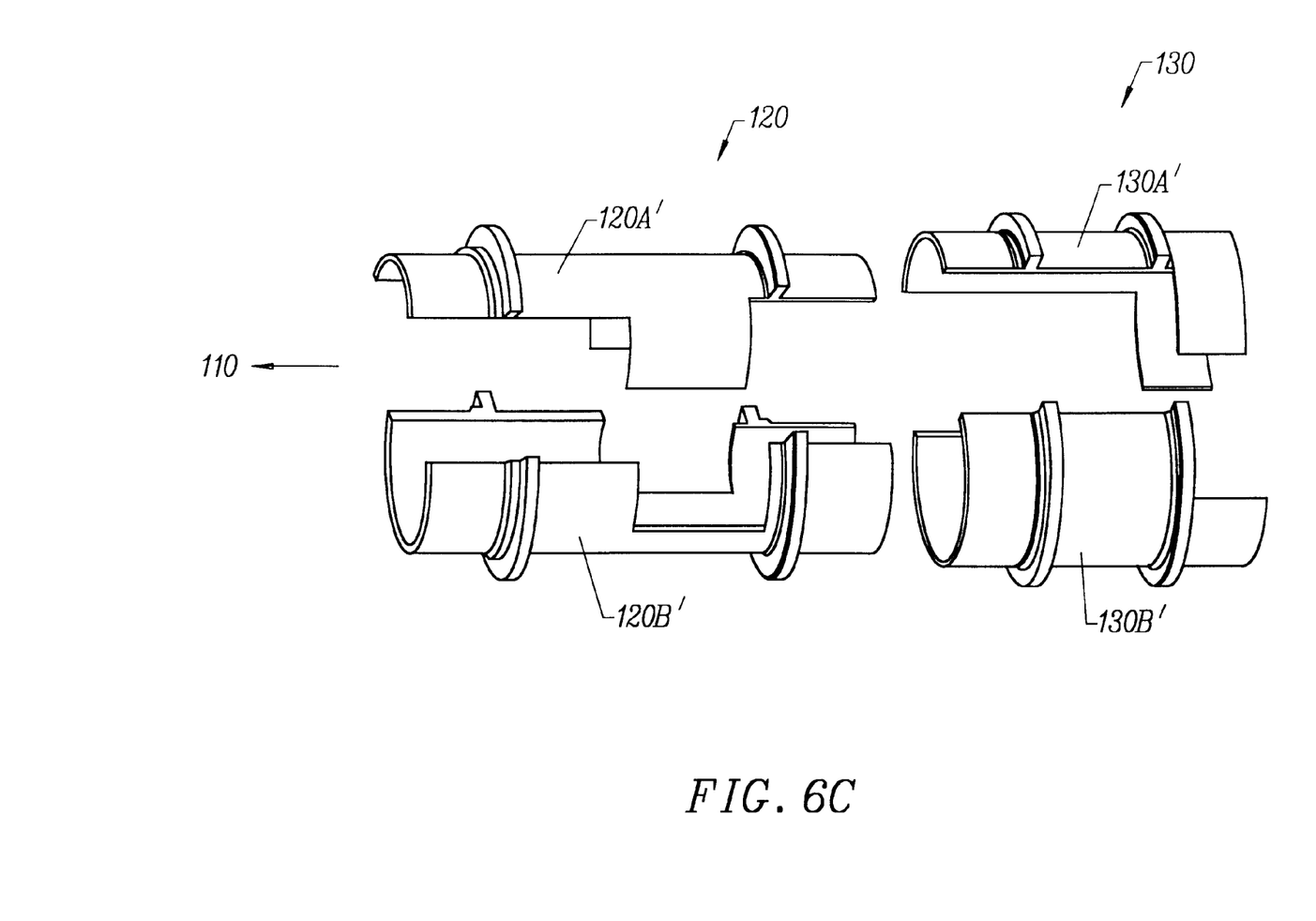
FIG. 6C is a breakaway perspective view of sections 120 and 130 from the configuration of FIG. 6B, according to the present invention.
Figure 6D:
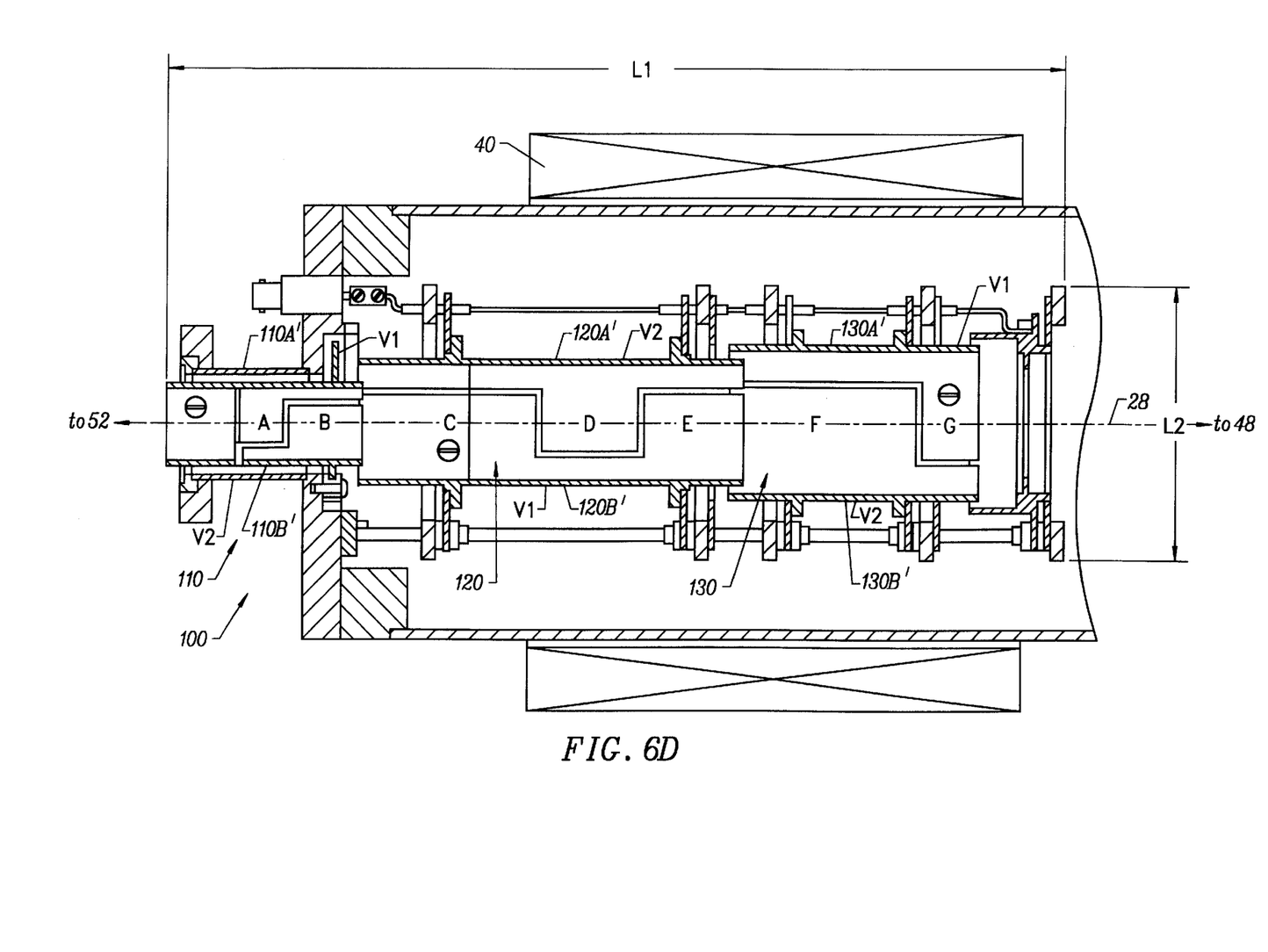
FIG. 6D is a cross-section showing the assembly of FIG. 6B.

As with the embodiment of FIG. 6A, three sections were found to be sufficient in implementing an electrode system 100 as shown in FIGS. 6B and 6C. Note however in FIG. 6B each electrode section is now preferably crenellated, and that the orientation of the crenellated sub-sections defines a helical twist. FIG. 6C is a breakaway perspective view of a portion of what is shown in FIG. 6B, namely depicting electrode members 120A', 120B' and 130A' and 130B'. FIG. 6D is a longitudinal cross-section of the electrode system shown in FIG. 6B, while FIGS. 7A–7G are transverse cross-sections of various electrode locations for the system shown in FIG. 6B. In FIGS. 6C. 6D, and 7A–7G, relative scaling has been preserved.

With respect to the cancellations, note in section 110 of FIG. 6B, the leftmost portion (denoted generally as "A") of the length of electrode member 110A' defines 240° arc, whereas the remaining length (denoted "B") of member 110A' defines 120° arc. At any cross-section there will be a complementary electrode member, and thus the left portion of the length of electrode member 110B' will define 120° arc whereas the right portion will define 240° arc. The complementary nature of the cancellations is readily seen in FIG. 6D, in which A and B again refer to the left and right portions of section 110.

Figures 7A, 7E:
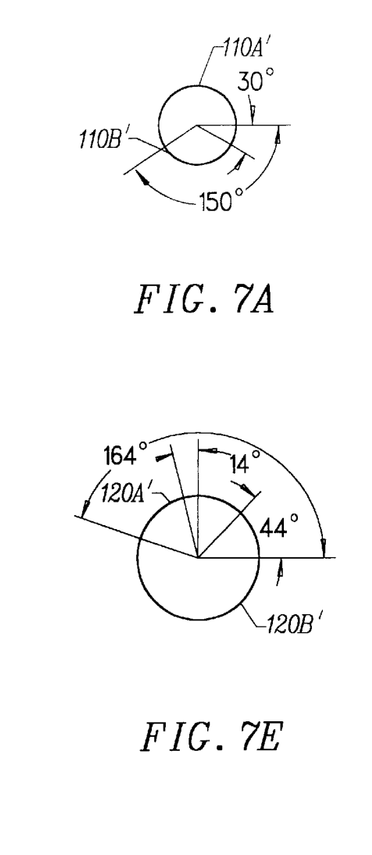
FIGS. 7A–7G are cross-sections of element arrays in the configuration of FIG. 6B, showing the progression of helical twisting, according to the present invention.
Figure 7B:
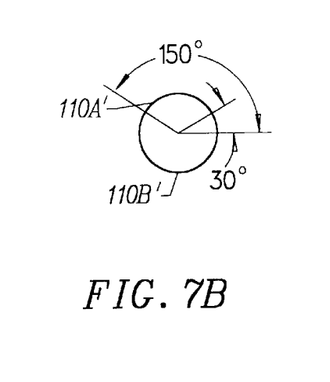

FIG. 7A is a cross-section through region A of section 110 and depicts the 240° and 120° arc lengths of members 110A', 110B' respectively. Similarly, FIG. 7B depicts the cross-section through region B of section 110, and shows the 120° and 240° respective arc lengths for 110A', 110B'.

Note in FIGS. 6B and 6C that center section 120 comprising electrode members 120A', 120B' preferably defines three cancellations at sections C, D, and E. In the particular embodiment described, the length of crenellation section C exceeded the length of crenellation section D or E. See also FIG. 6C.

Figure 7C:
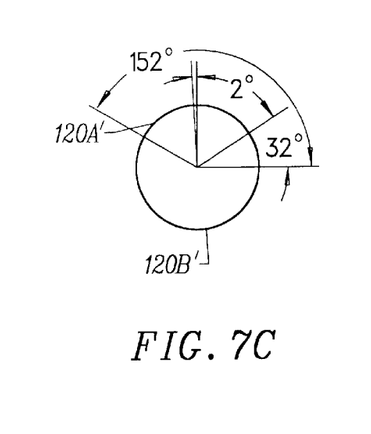
Figure 7D:
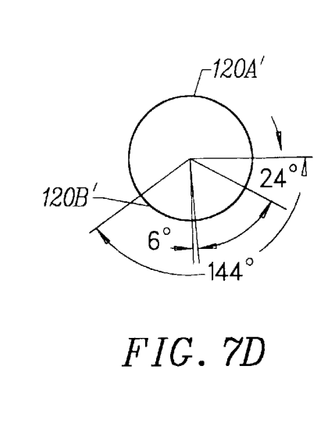

Bottom electrode member 120B' defines 240° arc through section C, 120° arc through section D, and 240° arc through section E. Upper electrode member 120A' is of course complementary, defining arc lengths 120°, 240°, 120° for sections C, D, and E respectively. Views through sections C, D, and E of section 120 are shown in FIGS. 7C, 7D, 7E respectively. Comparing FIG. 7B with FIG. 7C it is seen that 2° of helical twist is provided between region B (of section 110) and region C (of section 120). An additional 40 of twist is provided between region C and region D of section 120, as seen by comparing FIGS. 7C and 7D, e.g., section D is rotated a total of 6° relative to section A or B. FIG. 7E shows that additional twist is provided, 14° relative to section A.

Figure 7F:
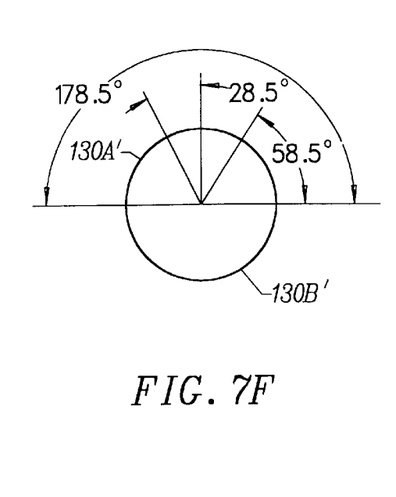
Figure 7G:
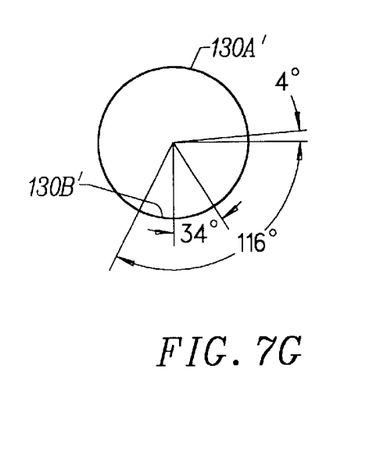

From FIGS. 6B and 6D it is seen that section 130 comprising elements 130A', 130B' has a leftmost portion F and a rightmost portion G. At section F, upper electrode member 130A' defines 120° arc and at section G 240° arc, while lower electrode member 130B' defines 240° and 120° respectively for sections F and G. FIGS. 7F and 7G indicate that helical offset at section F is 28.50° and at section G is 34° relative to sections A and B.

Recapitulating what is shown in FIGS. 6A–6D, in any cross-section one electrode member preferably described 240° arc and is coupled to a first potential, e.g., V1, while the other electrode member will describe a preferably 120° arc and will be connected to the other potential V2, e.g., ground. Further, as an approximation, the ratio between electrode radius and electron beam radius at any cross-section is preferably constant. In the two embodiments shown in FIGS. 6A and 6B, system 100 is located within solenoid coil 40, which dictated a maximum diameter dimension L2 of about 10 cm. The overall system length L1 was about 34 cm. Of course other geometries could instead be used.

The various helical offsets indicated by FIGS. 7A–7G were found to adequately compensate for the helical twist resulting from the magnetic field created by the magnetic solenoid used in the electron beam focusing system. Other electron beam scanner parameters also using a magnetic solenoid might require other angular offsets. It is understood that if the solenoid is absent (or present but set at zero strength), adjacent elements or sub-sections need not be progressivele helically twisted.

The preferred embodiment is the helically twisted crenellated configuration shown in FIGS. 6B–6D, and 7A–7G. In this embodiment system 100 fits within the dimensions of the system solenoid magnet 40, and thus has a maximum downstream dimension of about 10 cm. Understandably a greater number of shorter electrode sections or sub-sections, e.g., more than three sections or seven sub-sections, may improve multipole field cancellations, but at increased manufacturing cost.

In the configurations of FIGS. 6A and 6B, the first elements are coupled to one potential V1, and all second elements are coupled to a second potential V2 (ground), so that adjacent pairs of elements have reversed electric field orientation. For a given maximum V1 potential and optimum geometry, system 100 can produce dipole and decapole (generally odd multipole) electric fields as were produced by prior art electrode systems requiring multiple power sources and/or resistor dividers, and associated multiple electrical feedthroughs into the vacuum chamber. The 240° or 120° arc lengths were selected such that sextupole field strength remains at zero, as in the prior art electrode systems.

Unfortunately, in the present invention each configuration also produces quadrupole and octopole (generally even multipole) fields. The strengths of the even multipole fields are equal and alternate in sign so that their effects cancel as the sub-section cross-sections or fields alternate along the beam axis. Experimentation has demonstrated that adequate cancellation of multipole field effects occurs if the length of each element sub-section (or half-crenellation period, see FIG. 6A) is about equal to the electrode diameter.

As in the prior art, preferably a positive ion electrode ("PIE") 48, coupled to a large positive potential (e.g., +2 kV) is disposed coaxially downstream from system 100. So disposed, PIE 48 presents an axial field that prevents downstream-formed positive ions from migrating back upstream toward the electron gun.

To summarize, the present invention meets the shortcomings found in prior art systems. Operable from a single power source, the present invention requires fewer electrical feedthroughs into the vacuum chamber. Further, because a single power source may be used, all energized (e.g., coupled to high voltage V1) electrodes are directly connected, and thus all multipole fields remain proportional during any electric discharge. The single power source promotes safety and simplicity of design.

The use of complementary 240° and 120° element or sub-section arc lengths advantageously results in zero sextupole field. Since the electric field required for ion extraction needs to be inversely proportional to beam radius, a conical or stepped element configuration is used, which promotes cancellation of field effects. By providing elements or element sections with a helical twist that follows electron trajectories, more precise deflection cancellation is achieved. By alternating potential polarity on adjacent elements the effects of dipole fields are cancelled, and by providing alternating potential polarity and crenellated element edges, the effects of quadrupole and octopole fields are reduced.

In contrast to prior art systems, there is no net electron beam displacement, and no beam deflection or changes in focusing strength. This advantageously protects the X-ray emitting target from damage, and avoids damage to the overall computed tomography system and degradation of the images produced by the system. Further, the on-axis geometry of the electron beam leaving the present invention minimized aberration effects due to downstream beam-optical components. Finally, the present invention is relatively simple to assemble, align, and is robust in the field.

Modifications and variations may be made to the disclosed embodiments without departing from the subject and spirit of the invention as defined by the following claims. For example, although a single potential positive ion clearing electrode has been described for use in a scanning electron beam CT system, such electrode could be used in other applications as well, e.g., high current electron accelerator injectors, and possibly electron beam welders.

What is claimed is:

1. A single potential ion clearing electrode system useable with an electron beam computed tomographic scanning system including a solenoid coil coaxially mounted about an axis of said scanning system, the electrode system positioned substantially within said solenoid coil and comprising:

an array of at least three first elements, each of said first elements disposed along said axis and coaxial therewith and coupleable to a first node of an electrical power source; and an array of at least three second elements, each of said second elements disposed along said axis oppositely from a corresponding one of said first elements and coupleable to a second node of said electrical power source;

wherein in cross-section, each of said first elements and of said second elements define complementary arc length and have an element dimension that increases with position along said axis such that a ratio between element radius and electron beam radius is substantially constant.

2. The electrode system of claim 1, wherein:

said first node is at a potential whose absolute magnitude lies a range of about 800 V to about 2 kV; and said second node is at ground potential.

3. The electrode system of claim 1, wherein at any cross-section of said electrode system, one element defines an arc length of substantially 120° and an associated element defines an arc length of substantially 240°.

4. The electrode system of claim 3, wherein lengthwise adjacent elements alternate in one of (a) polarity of applied potential, and (b) arc length size.

5. The electrode system of claim 1, wherein each of said first elements and each of said second elements includes at least one sub-section that defines an arc length in cross-section selected from a group consisting of substantially 120° and substantially 240°.

6. The electrode system of claim 5, wherein lengthwise adjacent sub-sections alternate in one of (a) polarity of applied potential, and (b) arc length size.

7. The electrode system of claim 1, wherein:

said first node is coupled to a potential whose absolute magnitude lies in a range of about 800 V to about 2 kV, and said second node is coupled to ground; and said elements are configured such that application of said single potential produces dipole fields that alternate in orientation along said axis.

8. The electrode system of claim 3, wherein:

each of said elements includes at least one sub-section, and adjacent sub-sections in an element alternate substantially 180° with respect to orientation of arc length size such that effects on said beam due to net quadrupole and net octopole fields produced by said elements are self-cancelling.

9. The electrode system of claim 8, wherein said elements include crenellated edges.

10. The electrode system of claim 5, wherein:

an electron moving through said solenoid coil defines a helical trajectory; and at least two adjacent sub-sections in said electrode system are progressively helically twisted along said axis.

11. The electrode system of claim 1, wherein each of said first and said second elements have in cross-section a shape selected from a group consisting of (a) a substantially cylindrical shape, and (b) a substantially conical shape.

12. A single potential ion clearing electrode system useable with an electron beam computed tomographic scanning system including a solenoid coil coaxially mounted about an axis of said scanning system, the electrode system comprising:

at least three first elements disposed along said axis and coaxial therewith and coupleable to a first node of an electrical power source, each of said first elements having a shape selected from a group consisting of cylindrical and conical;

at least three second elements disposed along said axis oppositely from a corresponding one of said first elements and coupleable to a second node of said electrical power source, each of said second elements having a shape corresponding to a shape of an associated one of said first elements;

wherein in cross-section, each of said first elements and of said second elements have an element dimension that increases with position along said axis such that a ratio between element radius and electron beam radius is substantially constant;

wherein said electrode system is positioned substantially within said solenoid coil.

13. The electrode system of claim 12, wherein:

said first node is coupled to a potential whose absolute magnitude lies in a range of about 800 V to about 2 kV, and said second node coupled to ground potential;

said elements are configured such that adjacent pairs of associated first elements and second elements generate dipole fields that alternate along said axis;

wherein effects on said beam due to quadrupole and octopole fields substantially cancel.

14. The electrode system of claim 12, wherein at any cross-section an associated pair of a first element and a second element define complementary unequal arc lengths, one of said elements defining an arc length of substantially 120° and another of said elements defining an arc length of substantially 240°.

15. The electrode system of claim 12, wherein:

an electron moving through said solenoid coil defines a helical trajectory; and at least two adjacent elements in said electrode system are progressively helically twisted along said axis.

16. The electrode system of claim 15, wherein:

said elements include sub-sections; and said elements include crenellated edges.

17. A method of extracting positive ions from an electron beam generated by a computed tomographic scanning system that has a solenoid coil coaxially mounted about an axis of said scanning system, while ensuring safe focusing regimes, the method comprising the following steps:

(a) disposing within a length of said solenoid coil at least three first elements along said axis and coaxial therewith, said first elements having a substantially constant ratio between element radius and electron beam radius;

(b) coupling said first elements to a single power-source generated potential whose absolute magnitude ranges from about 800 V to about 2 kV;

(c) disposing within said length of said solenoid coil at least three second elements along said axis and coaxial therewith oppositely from a corresponding one of said first elements, said second elements sized to have said substantially constant ratio between element radius and electron beam radius; and (d) coupling said second elements to ground.

18. The method of claim 17, wherein:

step (a) includes forming said first elements with sub-sections having arc lengths of about 240° and about 120°, and rotating position of a 240° arc length sub-sections 180° relative to a lengthwise adjacent 240° sub-section; and step (b) includes forming said second elements with sub-sections having arc lengths of about 240° and about 120°, and rotating position of a 240° arc length sub-sections 180° relative to a lengthwise adjacent 240° sub-section;

wherein at any cross-section through an associated pair of first element and second element, one of said elements defines 240° arc length and a remaining one of said elements defines 120° arc length.

19. The method of claim 17, wherein step (a) and step (c) includes forming each of said elements in a manner selected from a group consisting of (i) each of said elements is formed as a length of constant radius cylinder, and (ii) each of said elements is formed with a conical shape.

20. The method of claim 17, wherein an electron beam moving through said solenoid coil defines a helical trajectory, and further including at least step selected from a group consisting of (i) step (a) includes progressively helically twisting at least two adjacent said elements, (ii) step (b) includes progressively helically twisting at least two adjacent said elements, (iii) step (a) includes forming at least a portion of said elements with a crenellated edge, and (iv) step (b) includes forming at least a portion of said elements with a crenellated edge.

* * * * *